United States Patent [19]

Burns

[11] Patent Number: 5,288,466
[45] Date of Patent: Feb. 22, 1994

[54] BLOOD MICROCOLLECTION TUBE ASSEMBLY

[75] Inventor: James A. Burns, Elizabeth, N.J.

[73] Assignee: Becton, Dickinson and Company, Franklin Lakes, N.J.

[21] Appl. No.: 32,771

[22] Filed: Mar. 16, 1993

Related U.S. Application Data

[63] Continuation of Ser. No. 716,225, Jun. 6, 1991, abandoned.

[51] Int. Cl.$^5$ .................... A61B 5/14; B01L 3/14; B65D 41/18; C12M 1/24
[52] U.S. Cl. .................... 422/102; 128/763; 128/767; 215/354; 215/355; 422/99; 435/296; 494/16
[58] Field of Search .................... 128/763–767; 215/321, 353, 354, 355; 422/99, 102; 435/296; 494/16

[56] References Cited

U.S. PATENT DOCUMENTS

| | | | |
|---|---|---|---|
| 2,287,746 | 6/1942 | Morton | 435/296 X |
| 3,005,564 | 10/1961 | Weichselbaum | 215/353 |
| 3,265,296 | 8/1966 | Mitchell | 494/16 |
| 3,419,179 | 12/1968 | Deuschle et al. | 220/306 |
| 3,481,712 | 12/1969 | Bernstein et al. | 422/102 |
| 3,574,333 | 4/1971 | Ohara | 215/295 |
| 3,706,306 | 12/1972 | Berger et al. | 128/764 X |
| 3,902,477 | 9/1975 | Gerarde | 128/2 F |
| 4,024,857 | 5/1977 | Blecher et al. | 128/2 F |
| 4,132,225 | 1/1979 | Whattam | 128/2 F |
| 4,215,700 | 8/1980 | Crouther et al. | 128/763 |
| 4,227,620 | 10/1980 | Conway | 215/355 |
| 4,250,893 | 2/1981 | White | 128/765 |
| 4,298,129 | 11/1981 | Stull | 215/224 |
| 4,390,111 | 6/1983 | Robbins et al. | 215/354 X |
| 4,397,318 | 8/1983 | Burns | 128/763 |
| 4,411,163 | 10/1983 | White | 73/864.02 |
| 4,576,185 | 3/1986 | Proud et al. | 128/760 |
| 4,620,549 | 11/1986 | Nugent | 128/763 |
| 4,799,599 | 1/1989 | Herrmann | 215/317 X |
| 4,804,096 | 2/1989 | Harding | 215/228 |
| 4,805,635 | 2/1989 | Korf et al. | 128/767 X |
| 4,845,038 | 7/1989 | Barr et al. | 435/296 |

Primary Examiner—James C. Housel
Assistant Examiner—Arlen Soderquist
Attorney, Agent, or Firm—Alan W. Fiedler

[57] ABSTRACT

A container assembly is provided for collecting capillary blood from a lanced wound. The container includes an integral lip for facilitating collection from the wound with the entire length of the container from lip to curved closed end being substantially the same large diameter for rapid collection before coagulation. The container includes an annular integral skirt enclosing the rounded bottom of the container to provide an annular stable surface for maintaining the container upright on a flat surface to facilitate subsequent examination of the collected blood. A cap for the assembly includes an annular space for receiving the top edge of the container in sealing engagement. This same annular space in the cap receives the annular bottom surface of the container skirt to join the two parts together when the container is open. The cap, in turn, includes an annular skirt for holding the open assembly in stable erect position on a flat surface. One form of the cap includes an expanded skirt for enclosing an annular flange extending from and adjacent to the top edge of the container, the latter being for the purpose of increasing the cooperating surfaces between the cap and the container top edge in the closed positions of the cap.

10 Claims, 4 Drawing Sheets

BLOOD MICROCOLLECTION TUBE ASSEMBLY

This is a continuation of copending application Ser. No. 07/711,225, filed on Jun. 6, 1991, which is now abandoned.

BACKGROUND AND STATEMENT OF THE INVENTION

This invention relates to a blood collection device for a microcollection container. More particularly, this invention relates to a blood collection device wherein the top edge of the container includes an integral scoop with a large engaging surface for engaging the puncture for collecting blood, and a substantially larger continuous container diameter throughout the length thereof for rapidly transferring the blood from the collecting tip into the container itself. Because of the relatively large engaging surface for engaging the puncture wound, the arrangement, in accordance herewith, does not require precise positioning of the scoop engaging surface in order to initiate and rapidly transfer a quantity of blood to the microcollection container.

Moreover, because of the continuously large diameter of the length of the container from the very tip of the scoop to the rounded bottom surface of the container, no venting is required in order to remove displaced air from the container in order to allow for the volume of blood flow into the container.

As will be appreciated by practitioners-in-the-art, analytical instrumentation has made it possible to carry out a variety of hematological diagnostic procedures on very small quantities of blood. Because of this, a patient's finger or earlobe, for example, may be punctured and a very small quantity of blood rapidly collected into a microcollection container for such test. Such arrangements obviate the need to withdraw venous blood from patients. However, such a collection arrangement must be such that the blood is rapidly collected prior to any coagulation thereof.

In the past, arrangements have been provided wherein a cap or top arrangement is configured to fit the top of a microcollection container with the top having an integral capillary tube for engaging the puncture and transferring blood to the container. However, with such an arrangement, the tip of the capillary tube must be arranged precisely adjacent the puncture wound and the entire apparatus must be so positioned that the blood flow is along the bottom surface of the tubular microcollection container, once the blood passes through the capillary tube in order to engage the surface of the container. Otherwise, if a precise positioning is not carried out, capillary action is not initiated or slowed, with subsequent clotting. A blood collector of the type utilizing a capillary tube is described in U.S. Pat. Nos. 4,024,856, issued May 24, 1977; 4,215,700, issued Aug. 5, 1980; 4,250,893, issued Feb. 17, 1981; 4,411,163, issued Oct. 25, 1983; and 4,132,225, issued Jan. 2, 1979.

Other representative blood microcollection tubes have been developed wherein the configuration of the opening of the top of the collection container is modified in order to receive and seal in engagement an elastomeric-type stopper for sealing and maintaining the collected blood specimen prior to examination. Representative of such structures include, for example, U.S. Pat. No. 3,902,477 and U.S. Pat. No. 4,227,620. Also, attention is called to FIG. 3 in U.S. Pat. No. 3,902,477 which teaches an integral bottom skirt 45 for stabilizing the container on a flat surface.

U.S. Pat. No. 4,576,185 teaches an integral collection lip for facilitating collection of blood from the wound. However, the container itself is of very small dimension and is difficult to handle. One of the problems with blood collection at this time, of course, is contamination from the specimen. The small configuration of the collection container taught and described in U.S. Pat. No. 4,576,185 is difficult to handle and is easily dropped or spilled during manipulation of the container for examination of the collected specimen or in the actual collection procedure. This is particularly true when a small baby, for example, is squirming while having a sample of blood obtained from a lanced sole of the foot.

Finally, U.S. Pat. No. 4,397,318 teaches a separate blood collection cap for a microcollection container with the cap including a scoop for collecting blood. The cap also includes a vent arrangement for allowing for the venting of air from the container displaced by the blood flowing into the container, so as to reduce any slowing up of the collection of the blood from the actual collection cap into the container. Such an arrangement, however, requires removal of the cap and the scoop and replacement with a sealing cap for transporting the collected specimen to a laboratory for examination.

With this invention, by contrast, and as noted above, a scoop arrangement is provided which is integral with the top edge of the collection container. No separate part is involved. Moreover, the container, including the area immediately adjacent the scoop, is of wide continuous diameter throughout the length of the container so that no air vent is required. Thus, the technician collects the blood from the wound which flows immediately into the container and then the cap provided can be placed in sealing engagement on top of the container.

The cap of the assembly of the invention includes an annular space for receiving the top edge of the container in sealing engagement. This annular space includes provision for incorporating therein the integral scoop on the top edge of the container as well. Part of the provisions of the present invention include the mating surfaces of the cap and the container. The configuration is such, as will be described in more detail below, as to provide substantial sealing between the cap and the container to preclude any blood leakage.

Moreover, the annular space utilized for receiving the top edge of the container also is useful for receiving sequentially the bottom skirt integral with the bottom surface of the container so that the cap may be placed on the bottom surface when the technician opens the container for examination of the specimen. This same positioning may be utilized by the technician during the collection procedure in order for the cap to be readily available for replacement on the open end of the container once collection has taken place.

A further feature of the present invention is a snap-lock feature with the inner seal of the cap relative to the container. Moreover, because of the arrangement of the seal of the cap with the container, any blood on the seal of the cap will not come in contact with the container when the cap is stored on the bottom of the container. Finally, because of the wide open mouth of the lip of the container in this invention, blood flows into the tube at any collection angle, and the dimension of the tube is of a size which makes it much easier to handle in the general sense than the very narrow microcollection tubes currently in use.

DETAILED DESCRIPTION OF THE INVENTION

Figure 1:
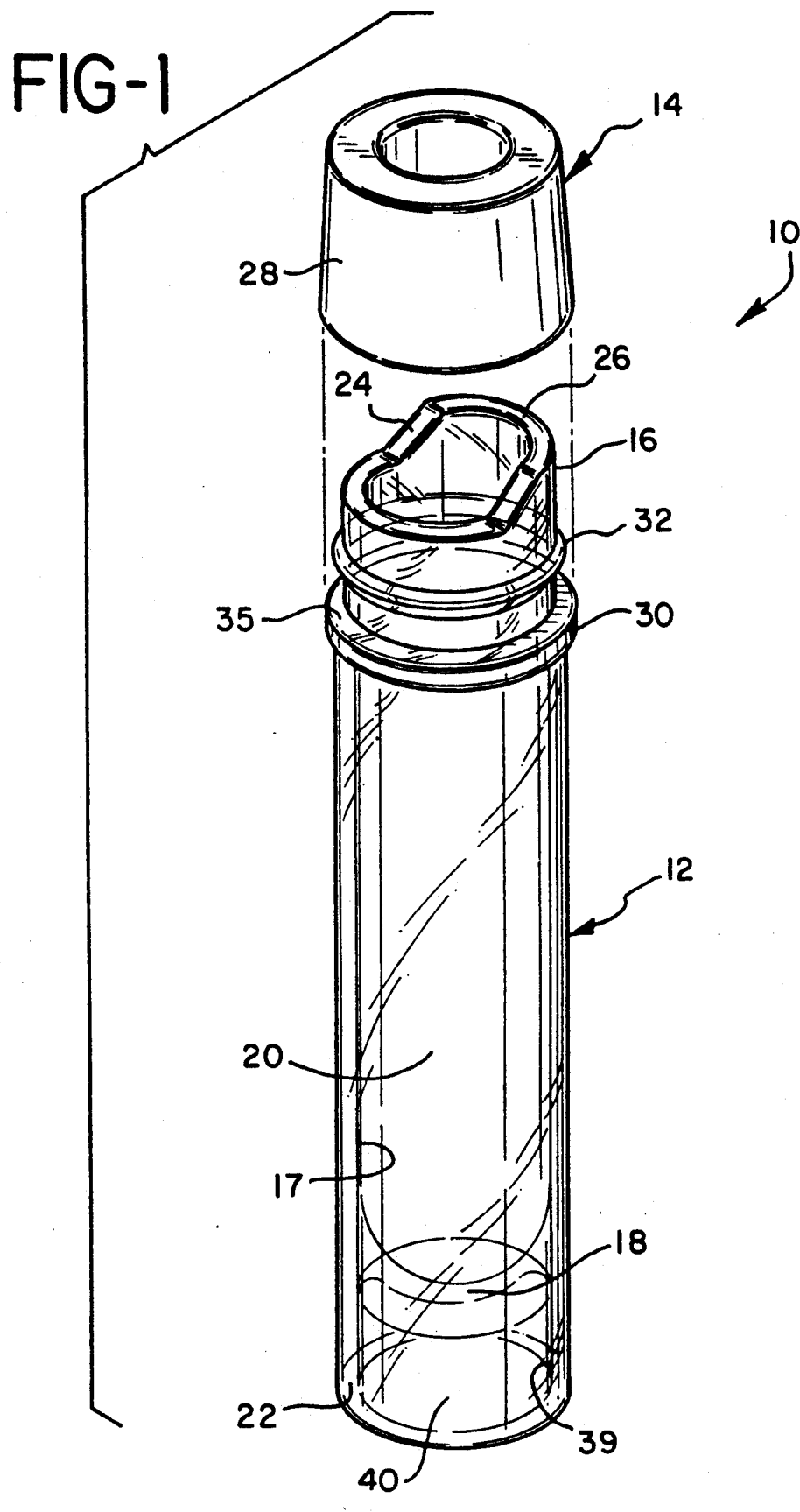
FIG. 1 is an exploded perspective view of a first embodiment of a blood collector assembly for this invention.

Referring to the drawings in which like reference characters refer to like parts throughout the several views thereof, FIG. 1 illustrates a first embodiment of the invention as employed in a blood collection assembly with the cap positioned in place, sealing the open end of the container of the assembly.

In FIG. 1 the device or assembly generally designated 10 includes a container 12 and a cap 14. The illustration shows the configuration of the container 12 and its mating surfaces with the cap 14. Thus, container 12 includes a blood collection compartment 20 having an open end 16 and a rounded closed end 18. Container 12 includes an integral annular skirt 22 having an internal surface 39 which defines a compartment area 40 for receiving a portion of the cap, to be discussed in more detail below.

Figure 2:
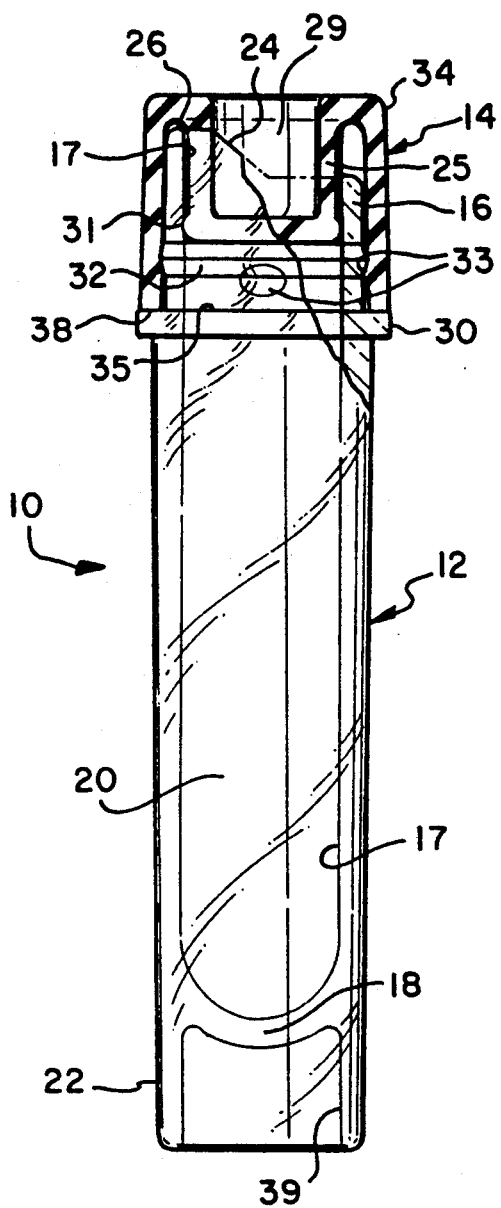
FIG. 2 is a side elevational view, partially in section, for the first embodiment of a blood collector assembly of FIG. 1 in its sealed orientation with a cap for this invention.
Figure 3:
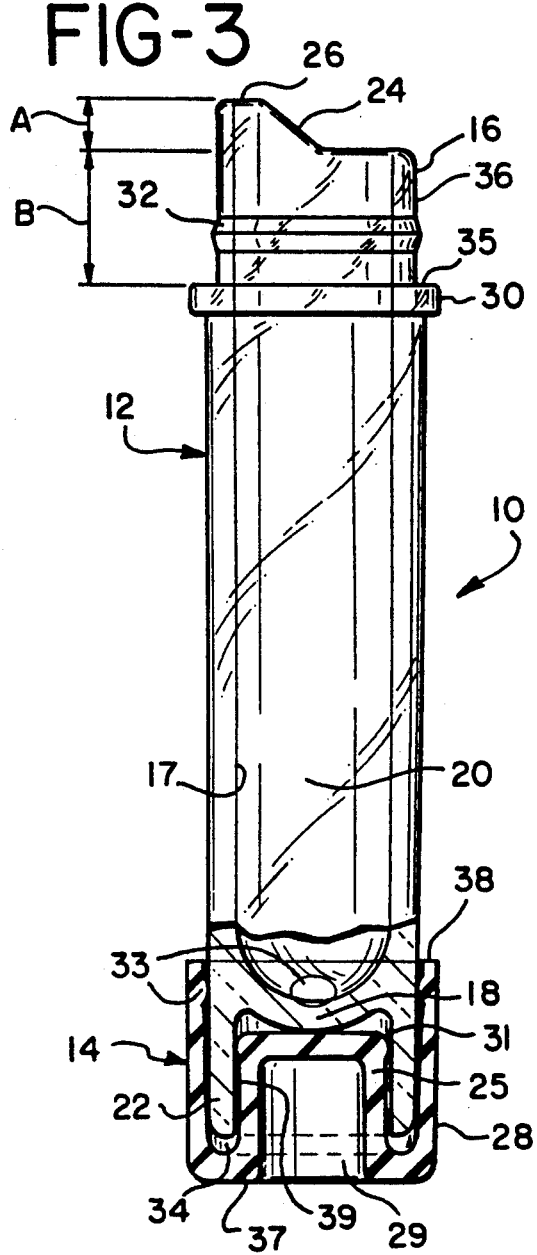
FIG. 3 is a side elevational view, partially in section, of a blood collector assembly of FIG. 1 in its unsealed orientation with the cap mounted on the bottom of the blood collector for this invention.
Figure 4:
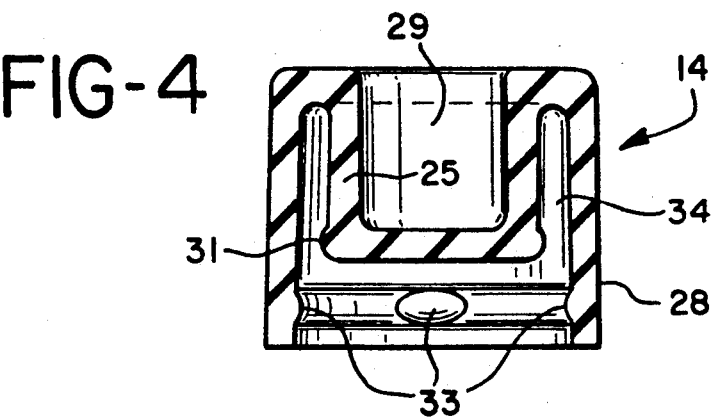
FIG. 4 is an enlarged cross sectional view of the cap in the first embodiment of FIG. 1.
Figure 5:
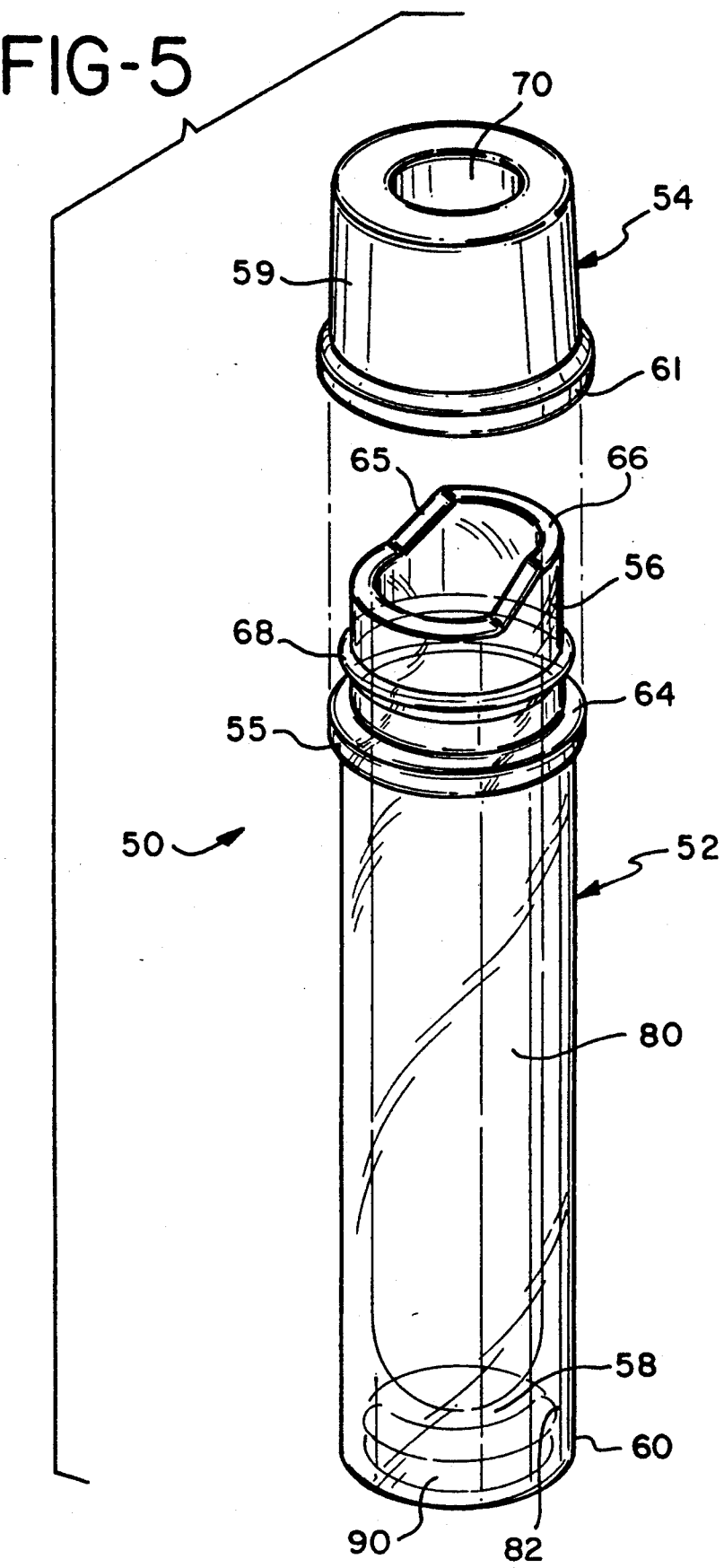
FIG. 5 is an exploded perspective view of a second embodiment of a blood collector assembly for this invention.

As can be seen in FIGS. 1 and 3, the open end 16 of container 12 includes an integral lip portion 24 with a receiving edge 26 to be placed adjacent a lanced wound for collection of blood rapidly through the broad dimensioned container 12. This facilitates the collection of blood into and to the bottom surface of the closed end 18 of container 12. As can be seen in FIGS. 1, 2, 3 and 4, cap 14 includes an annular outer skirt 28 and an inner annular inverted skirt portion or cup 25. The two are spaced from each other to define an annular space 34 (FIG. 2). Space 34 receives the upper annular receiving edge 26 of the open end 16 of container 12.

The inner annular skirt portion 25 includes an annular ring 31 for sealing against the internal surface 17 of the upper open end 16 of container 12. On the internal surface of skirt 28 of cap 14, a plurality of circumferentially spaced protrusions 33 are positioned to engage in snap-lock engagement with the annular integral sealing ring 32 positioned on the outer surface of container 12. Also, ring 32 seals and abuts against the internal surface 39 of the skirt 28 of cap 14. The protrusions 33 bear against the bottom edge of ring 32 for holding the cap in the closed position.

Finally, as shown in FIG. 3, an annular integral flange 30 is positioned around the outer surface of container 12 adjacent a mating surface 36 extending from flange 30 to the open end thereof for receiving the bottom edge 38 (FIG. 2) of cap 14. 31 seals against an upper surface 35 of flange 30 for providing yet another cooperative sealing surface between cap 14 and container 12.

Thus, the user, when ready to make a collection of blood from a lanced wound, removes cap 14 from its sterile sealing engagement on a container 12 and places the cap in a position substantially as shown in FIG. 3. In the final seated position of cap 14 on skirt 22, protrusions 33 bear against the outer surface of skirt 22, while ring 31 clears, slightly, internal surface 39.

The idea is to hold cap 14 for ready grasping once a blood specimen has been collected into the compartment or chamber 20 of container 12. Thus, the collection of a blood specimen is made and cap 14 is removed from skirt 22 on the bottom of container 12 and placed in sealing engagement over the open end 16 of container 12 for transport to a laboratory for examination of the specimen. Mating surface 36 has sealing ring 32 thereon and a length B longer than a length A of integral lip portion 24 to minimize the flow of blood down mating surface 36 and onto flange 30. Bottom edge 38. It should be understood that during this handling procedure, because of the larger diameter of assembly 10 the assembly is much easier to handle. Moreover, the lab technician, once receiving assembly 10 may readily utilize the skirt 22 for standing the assembly 10 on a flat surface.

Figure 6:
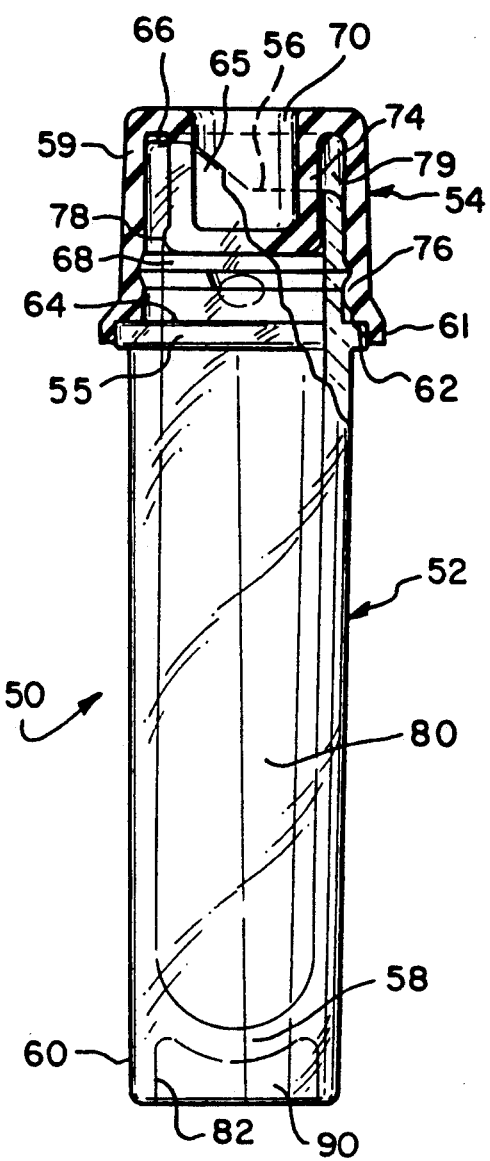
FIG. 6 is a side elevational view, partially in section, for the second embodiment of a blood collector assembly of FIG. 5 in its sealed orientation with a cap for this invention.
Figure 7:
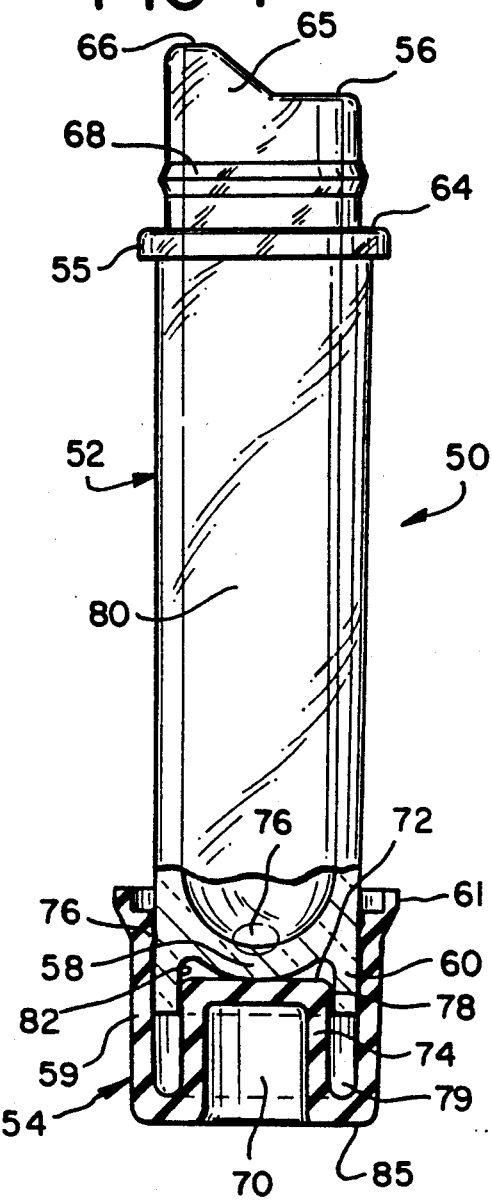
FIG. 7 is a side elevational view, partially in section, of a blood collector assembly of FIG. 5 in its unsealed orientation with the cap mounted on the bottom of the blood collector for this invention.

Referring now to FIGS. 5, 6, 7 and 8, a further embodiment of the invention is shown in the form of an assembly 50. With this embodiment, which is substantially the same as the embodiment shown in FIGS. 1, 2, 3 and 4 with variations, the skirt 60 on the bottom of container 52 is of shorter dimension, and the internal surface 82 of skirt 60 defines space 90. Thus, when cap 54 is positioned on the bottom of container 52, for example, the bottom surface of the rounded portion 58 of chamber 80 may engage the top surface 72 of the internal annular portion 74 of cap 54 in its final position, as shown in FIG. 7. The legs of skirt 60 do not move into the annular space 79 to the same extent as with the embodiment shown in FIGS. 1, 2, 3 and 4.

Figure 8:
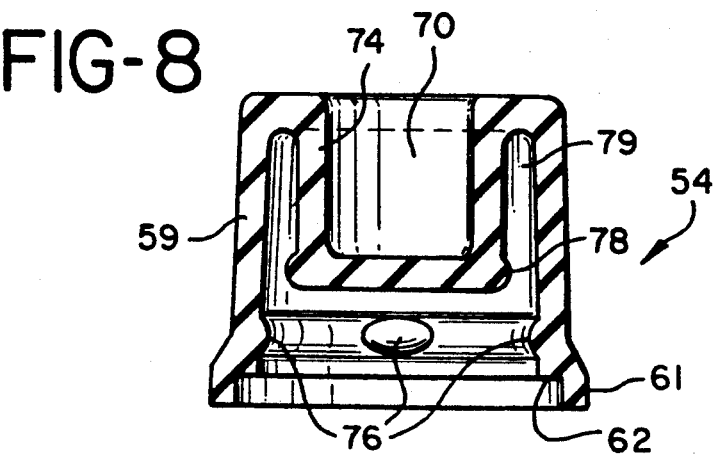
FIG. 8 is an enlarged cross sectional view of the cap in the second embodiment of FIG. 5.

Referring now to cap 54 in FIG. 8, the annular outer skirt 59 of cap 54 includes an angular annular flange 61 which extends outwardly and engages flange 55 formed integrally on the outer surface of container 52 in the same manner as flange 30 in the embodiment of FIGS. 1, 2, 3 and 4. Because of this, the outer flange 61 of skirt 59 provides a larger engagement of surfaces 62 of cap 54 with the surface 64 of flange 55. The engaging surfaces include the top surface 64 of flange 55, as is clearly shown in FIG. 7 together with the annular outer edge thereof. This insures more sealing surface engagement for the cap 54 relative to the container 52 in the assembly 50. It should be kept in mind, however, that flange 61 does not cover flange 55 completely, as shown in FIG. 6. There is less than 0.010 inches coverage, so that when the capped assembly is centrifuged, the load is on flange 55 and the cap is not loosened.

In this connection, cap 54 includes circumferentially spaced protrusions 76 for snap engagement with the annular ring 68 integral with container 52 and adjacent the top open edge 56 thereof. Also, cap 54 includes annular seal 78 for bearing against the internal surface of container 52. Container 52 includes a closed bottom end 58 for defining a chamber 80 for receiving collected blood therein. Container 52 also includes an integral lip 65 with a collection edge 66 for being placed against a lanced wound for the rapid collection of blood prior to coagulation thereof.

The technician utilizes the embodiment shown in FIGS. 5, 6, 7, and 8 in the same manner as described above for the embodiments described in FIGS. 1, 2, 3 and 4. Once collection has been made, and a stabilized assembly is obtained the internal surfaces of the cap are not exposed to the person handling the assembly. For subsequent examination, the flat surface 85 of cap 54 provides proper stability for the assembly 50. The same thing is true of the flat surface 37 for assembly 10. As will be understood by practitioners-in-the-art, however, the assemblies 10 and 50 both are configured to allow for stable standing of the assembly with the caps closing the open ends of their respective containers 12 and 52. That is, annular skirt 60 on the assembly 50 provides a surface for allowing the assembly to stand in a stabilized position on a flat surface in the closed position thereof. The same thing is true of the annular skirt 22 on container 12 in the embodiment shown in FIGS. 1, 2, 3 and 4. The annular internal portion 25 of the embodiment in FIG. 1 of cap 14 defines an open non-used area 29, while the same is true of area 70 in the assembly 50 embodiment, as shown in FIGS. 5, 6, 7 and 8.

The microcollection assembly of the invention may be made of a clear molded thermoplastic material so that the specimen collected may be readily viewed. Representative materials include, for example, polyethylene, polypropylene and polyvinyl chloride. The microcollection container may incorporate a hydrophilic material or a silicon may be applied to the internal surface thereof for enhancing the flow of blood introduced into the container.

While the forms of apparatus herein described constitute preferred embodiments of the invention, it is to be understood that the invention is not limited to these precise forms of apparatus, and that changes may be made therein without departing from the scope of the invention which is defined in the appended claims.

For example, while the cap has been described above as being of a transparent material, it is within the purview of the invention to provide caps which are not transparent but colored to define specific forms of blood microcollection containers containing materials for one reason or another or for defining the kind of examination to be conducted on the specimen collected. Also, it should be noted that the dimensions of the container are such as to provide space for labeling which may be important for identifying the collected specimens. The very small dimensions of microcollection containers now in use prevent proper labeling of specimens for this reason.

What is claimed:

1. A capillary blood specimen collection assembly for collecting blood comprising:
   an elongated blood collection container, said container defining a tubular blood collection chamber;
   said chamber having an annular open end and a closed end;
   an integral lip coaxially extending from said open end of said container;
   an annular integral cap seating flange having a top surface and an annular outer edge, said top surface extending outwardly from said container and spaced from said open end;
   an annular integral cap locking abutment extending outwardly from said container between said open end and said annular cap seating flange;
   an integral annular skirt extending from a bottom edge of said container and surrounding said closed end;
   a sealing cap for sealing said open end of said container;
   said sealing cap having an annular outer skirt with a flat bottom surface for sealing engagement with a top surface of said annular cap seating flange;
   said annular outer skirt having an angled integral extension extending from said flat bottom surface for receiving therein said top surface and a portion of said annular outer edge of said annular cap seating flange when said cap is placed over said open end, said extension not extending beyond said annular cap seating flange so that force is only applied to the bottom of said annular cap seating flange and no loosening force is applied to said extension when the capped assembly is centrifuged;
   said annular outer skirt having a plurality of circumferentially spaced protrusions positioned around said inner surface for engaging said annular cap locking abutment in a releasable snap-lock engagement when said cap is placed over said open end;
   said sealing cap having a cup-shaped inner portion contained within said cap and surrounded by said annular outer skirt; and
   said cup-shaped inner portion having an annular inner skirt spaced from said outer skirt on said cap to define an annular receiving space for receiving, alternatively, said container open end and said skirt of said container,
   wherein said cup-shaped inner portion is received and enclosed within said skirt of said container when said receiving space receives said skirt to prevent said cup-shaped inner portion from being contaminated before being placed in said open end of said container and to contain any blood on said cup-shaped inner portion within said skirt at the bottom of said container when said cap is removed from said open end and stored on the bottom of said container.

2. The assembly of claim 1 further comprising an annular sealing abutment extending outwardly from said cap inner skirt for providing a primary seal against an inner surface of said blood collection chamber when said cap is placed over said open end and is locked in place by said protrusions being in snap-lock engagement with said annular cap locking abutment.

3. The assembly of claim 1, wherein said annular outer skirt on said cap is longer than said annular inner skirt of said cup-shaped inner portion on said cap.

4. The assembly of one of claim 1, further comprising:
   an annular sealing abutment extending outwardly from said cap inner skirt, whereby said annular sealing abutment fits inside said integral annular skirt extending from the bottom edge of said container when said cap is placed on the bottom of said container.

5. A capillary blood specimen collection assembly for collecting blood comprising:

an elongated blood collection container including a blood collection chamber having an annular open end, an integral lip coaxially extending from said open end and an annular integral cap seating flange extending outwardly from said container and spaced from said open end; and a sealing cap having a top and a bottom for sealing engagement with said open end of said container, said cap having an annular outer skirt extending from the top to the bottom of said cap and a cup-shaped inner portion surrounded by said annular outer skirt and extending from the top toward the bottom of said cap, said cup-shaped inner portion having an annular bottom surface, and said annular outer skirt extending beyond said annular bottom surface of said cup-shaped inner portion and having an angled integral extension extending from its bottom for receiving therein a top surface and a portion of an annular outer edge of said annular integral cap seating flange to provide a larger sealing surface engagement when said cap is placed over said open end, wherein said extension does not extend beyond said annular cap seating flange so that force is only applied to the bottom of said annular cap seating flange and no loosening force is applied to said extension, when the capped assembly is centrifuged.

6. The assembly of claim 5, further comprising:
an annular sealing abutment extending outwardly from said annular bottom surface of said cup-shaped inner portion, whereby said annular sealing abutment seals against an inner surface of said blood collection chamber when said cap is placed over said open end.

7. The assembly of claim 5, wherein said annular outer skirt on said cap extends sufficiently beyond said annular bottom surface of said cup-shaped inner portion to prevent contamination of said annular bottom surface when said cap is removed from said open end of said container.

8. The assembly of claim 5, further comprising:
a plurality of circumferentially spaced protrusions positioned around an inner surface of said cap outer skirt; and
an annular cap locking abutment extending outwardly from said container near said open end and engaging said plurality of protrusions in a snap-lock engagement when said cap is placed over said open end.

9. The assembly of claim 5, further comprising:
an integral annular skirt extending from a bottom edge of said container.

10. The assembly of one of claim 9, further comprising:
an annular sealing abutment extending outwardly from said cap inner skirt, whereby said annular sealing abutment fits inside said integral annular skirt extending from the bottom edge of said container when said cap is placed on the bottom of said container.

* * * * *